(12) United States Patent
Kovacevic

(10) Patent No.: US 11,995,594 B2
(45) Date of Patent: May 28, 2024

(54) MANAGING TECHNICAL PROCESS DATA

(71) Applicant: Alecson Feld Australia Pty Ltd, Bowral (AU)

(72) Inventor: Aleksandar Kovacevic, Bowral (AU)

(73) Assignee: Alecson Feld Australia Pty Ltd, Bowral (AU)

( * ) Notice: Subject to any disclaimer, the term of this patent is extended or adjusted under 35 U.S.C. 154(b) by 0 days.

(21) Appl. No.: 17/226,617

(22) Filed: Apr. 9, 2021

(65) Prior Publication Data

US 2022/0058536 A1 Feb. 24, 2022

Related U.S. Application Data

(63) Continuation of application No. 15/766,499, filed as application No. PCT/AU2016/050946 on Oct. 7, 2016, now abandoned.

(Continued)

(30) Foreign Application Priority Data

Oct. 9, 2015 (AU) ................................ 2015904128

(51) Int. Cl.
*G06Q 10/06* (2023.01)
*G06Q 10/00* (2023.01)
(Continued)

(52) U.S. Cl.
CPC ......... *G06Q 10/0635* (2013.01); *G06Q 10/00* (2013.01); *G06Q 10/0637* (2013.01);
(Continued)

(58) Field of Classification Search
CPC .................................................. G06Q 10/06
See application file for complete search history.

(56) References Cited

U.S. PATENT DOCUMENTS 6,571,282 B1 * 5/2003 Bowman-Amuah ........................ H04L 67/303
719/329
6,789,252 B1 * 9/2004 Burke ....................... G06F 8/10
717/103

(Continued)

FOREIGN PATENT DOCUMENTS

WO WO-2007044383 A2 * 4/2007 ......... G06Q 10/0631

OTHER PUBLICATIONS

Basel Committee on Banking Supervision, Principles for effective risk data aggregation and risk reporting, Bank for International Settlements 2013. (Year: 2013).*

(Continued)

*Primary Examiner* — Kurtis Gills
(74) *Attorney, Agent, or Firm* — Crowell & Moring LLP

(57) ABSTRACT

This disclosure relates to computer systems for managing technical process data. An input port receives technical process data from multiple technical process experts, wherein the technical process data relates to a technical impact of one or more physical events on a continuity of a technical operation. A database stores the technical process data. A processor validates the technical process data and initiates a bidding process. The processor further physically presents the technical process data in the bidding process, receives bidding data from multiple bidding client computer systems associated with multiple bids, selects one of multiple bids based on the bidding data, and stores an association between the bidding data associated with the one of the multiple bids and the technical process data on the database.

20 Claims, 11 Drawing Sheets

Related U.S. Application Data

(60) Provisional application No. 62/365,360, filed on Jul. 21, 2016.

(51) Int. Cl.

| | | |
|---|---|---|
| *G06Q 10/0635* | (2023.01) | |
| *G06Q 10/0637* | (2023.01) | |
| *G06Q 10/0639* | (2023.01) | |
| *G06Q 10/10* | (2023.01) | |
| *G06Q 30/08* | (2012.01) | |
| *G16H 40/20* | (2018.01) | |

(52) U.S. Cl.
CPC ......... *G06Q 10/0639* (2013.01); *G06Q 10/10* (2013.01); *G06Q 30/08* (2013.01); *G16H 40/20* (2018.01); *G06Q 2220/10* (2013.01)

(56) References Cited

U.S. PATENT DOCUMENTS

| | | | |
|---|---|---|---|
| 7,069,234 B1 * | 6/2006 | Cornelius | G06Q 40/00 705/26.8 |
| 7,840,473 B2 | 11/2010 | Kraehenbuehl et al. | |
| 8,645,194 B1 | 2/2014 | Lehmann et al. | |
| 2004/0260703 A1 | 12/2004 | Elkins et al. | |
| 2007/0087756 A1 * | 4/2007 | Hoffberg | G06Q 20/065 455/450 |
| 2009/0177500 A1 | 7/2009 | Swahn | |
| 2013/0024235 A1 * | 1/2013 | Willems | G06Q 10/06 705/7.23 |
| 2014/0310243 A1 * | 10/2014 | McGee | G06F 16/27 707/639 |

OTHER PUBLICATIONS

Gillespie, Clay Michael, "How Blockchain Technology Could Revolutionize the $1.1 Trillion Insurance Industry," https://insidebitcoins.com/news/how-blockchain-technology-could-revolutionize-the-1-1-trillion-insurance-industry/28516.

International Search Report for International application No. PCT/AU2016/050946, dated Nov. 1, 2016.

Written Opinion of the International Searching Authority for International application No. PCT/AU2016/050946, dated Nov. 1, 2016.

* cited by examiner

| Critical Function A (Name) | Impact within 3hrs | Impact within 3hrs – 8hrs | Impact within 24hrs | Impact within 48hrs | Impact within 72hrs | Total Impact in $ | Percentage of Impact comparing to Company-wide impact |
|---|---|---|---|---|---|---|---|
| 702 | 704 | 706 | 708 | 710 | 712 | 714 | 716 |
| | | | | | | | |
| | | | | | | | |
| | | | | | | | |
| | | | | | | | |

Observations: 718

Fig. 7

| Critical Function A (Name) | Impact within 3hrs | Impact within 3hrs – 8hrs | Impact within 24hrs | Impact within 48hrs | Impact within 72hrs | Total Impact in $ | Percentage of Impact comparing to Company-wide impact |
|---|---|---|---|---|---|---|---|
| Impact Category #1 | 120,000 | 200,000 | 450,000 | 800,000 | 2,500,000 | 4,070,000 | 3% |
| Impact Category #2 | 0 | 600,000 | 150,000 | 0 | 0 | 750,000 | < 1% |
| Impact Category #3 | 400,000 | 400,000 | 800,000 | 2,000,000 | 15,000,000 | 18,600,000 | 20% |
| Reputational Impact | Insignificant | | Greatest Impact | | | Significant, as it may cause a high loss of customers: $ '000 (TBA) | |

Observations:
1 – at least 80% of the impact first hits within 3-8hrs. Total impact is less than $5mil, suggesting that is not as critical as other within the organisation.
2 – Impact less than $1mil may be considered less-critical.
3 – Highest losses expected in this category, hence, for Quantifiable impact under $500K, suggested RTO (recovery time objective) is 72hrs and for Reputational impact is within the first 9-24hrs.

Fig. 8

IMPACT DATA RELATED TO GENERATOR — 902

| Critical Function A (Name) | Impact within 3hrs — 702 | Impact within 3hrs – 8hrs — 704 | Impact within 24hrs — 708 | Impact within 48hrs — 710 | Impact within 72hrs — 712 | Total Impact in $ — 714 | Percentage of Impact comparing to Company-wide impact — 716 |
|---|---|---|---|---|---|---|---|
| | | | | | | | |
| | | | | | | | |
| | | | | | | | |
| | | | | | | | |

Observations: ⎯ 718

REGISTRATION

Organisation:

Insurance or Reinsurance: [____] 1402 ?
Industries interested in [____] 1404

Geographical exposure: [____] 1406
(please select/tick as appropriate areas/territories)
Preferred Password: [____] 1408

| Company XYZ | Total BIA Exposure($) | Recovery options tested (Y/N) | Full BCM Plan in place (Y/N) |
|---|---|---|---|
| STC Generator | $5mil | Yes for the full recovery within 72hrs | Yes, for entire organisation |

How often do you conduct exercises / BCM Plan Tests: _____
(monthly, quarterly, semi-annually...)

Fig. 15

MANAGING TECHNICAL PROCESS DATA

CROSS-REFERENCE TO RELATED APPLICATIONS

The present application is a continuation of U.S. patent application Ser. No. 15/766,499, which has a 371(c) date of Apr. 6, 2018, which is the U.S. National Stage application of PCT Application No. PCT/AU2016/050946, filed on Oct. 7, 2016, designating the United States, which claims the benefit of U.S. Provisional Application 62/365,360, filed Jul. 21, 2016, and which claims priority to Australian Patent Application 2015904128, filed Oct. 9, 2015, of which the contents of all such applications are incorporated herein by reference.

TECHNICAL FIELD

This disclosure relates to managing technical process data. In particular, but not limited to, this disclosure relates to a dedicated data entry system, data processing system and data provisioning system.

BACKGROUND

Many larger corporations perform a large number of technical processes. Examples of technical processes may include electricity back-up processes of hospitals using power generators, production machinery running a production process or drive trains of cargo ships operating globally. However, it is often difficult for these corporations to collect process and provision data on these technical processes.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

A computer system for processing technical process data comprises:
  an input port to receive technical process data from multiple technical process experts, wherein the technical process data relates to a technical impact of one or more physical events on a continuity of a technical operation;
  a database to store the technical process data;
  a processor
  to validate the technical process data and initiate a bidding process,
  to physically present the technical process data in the bidding process,
  to receive bidding data from multiple bidding client computer systems associated with multiple bids,
  to select one of multiple bids based on the bidding data, and
  to store an association between the bidding data associated with the one of the multiple bids and the technical process data on the database.

Since the computer system collects technical process data from technical process experts the impact of the physical events is characterised more accurately than in cases where actuaries make the assessment based on abstract business data. This becomes a particular advantage in relation to the bidding process as bidding participants connected to the computer system can get a better understanding of the character of the technical process data.

The input port may be connected to multiple client computer systems, each of the multiple client computer systems comprising:
  a processor to generate a user interface for receiving technical process data that relates to a technical impact of one or more physical events on a continuity of a technical operation;
  a data port to send the technical process data to the above computer system.

The processor may be configured to generate a user interface that allows the technical process expert to enter technical process data, wherein the user interface is specific to that technical process expert.

The technical process data may relate to a business continuity analysis or a business impact analysis.

Validating the technical process data may comprise validating the technical process data against ISO 22317.

Validating the technical process data may comprise validating the technical process data against ISO/TS 22317: 2015.

The processor may further be configured to determine an aggregate value of multiple technical operations based on the respective technical process data.

The step of physically presenting the technical process data may comprise generating a user interface comprising input elements to filter a subset of multiple technical operations.

The computer system may be a bidding server.

The processor may further be configured to operate a blockchain to facilitate distributed communication to the multiple bidding client computer systems.

The processor may further be configured to verify the technical process experts.

A computer implemented method for processing technical process data that relates to a technical impact of one or more physical events on a continuity of a technical operation comprises:
  validating the technical process data and initiate a bidding process;
  physically presenting the technical process data in the bidding process;
  receiving bidding data from multiple bidding client computer systems associated with multiple bids;
  selecting one of multiple bids based on the bidding data; and
  storing an association between the bidding data associated with the one of the multiple bids and the technical process data on the database.

Software when installed on a computer causes the computer to perform the above method.

A computer network for processing technical process data comprises:
  the computer system above;
  multiple client computer systems, each comprising:
    a processor to generate a user interface for receiving technical process data that relates to a technical impact of one or more physical events on a continuity of a technical operation;

a data port to send the technical process data to the above computer system.

The processor of each of the multiple client computer systems may be configured to operate a blockchain for sending the technical process data.

Optional features described of any aspect of method, software or computer system, where appropriate, similarly apply to the other aspects also described here.

BRIEF DESCRIPTION OF DRAWINGS

An example will be described with reference to the following figures:

FIG. 7 illustrates a user interface to allow the technical expert to enter technical process data.

FIG. 8 illustrates the user interface in FIG. 7 with technical process data entered.

FIG. 9 illustrates a data entry user interface that is specific to a particular technical expert.

FIG. 14 illustrates a registration user interface for the financial manager.

FIG. 15 illustrates a sample report.

DESCRIPTION OF EMBODIMENTS

Figure 1:
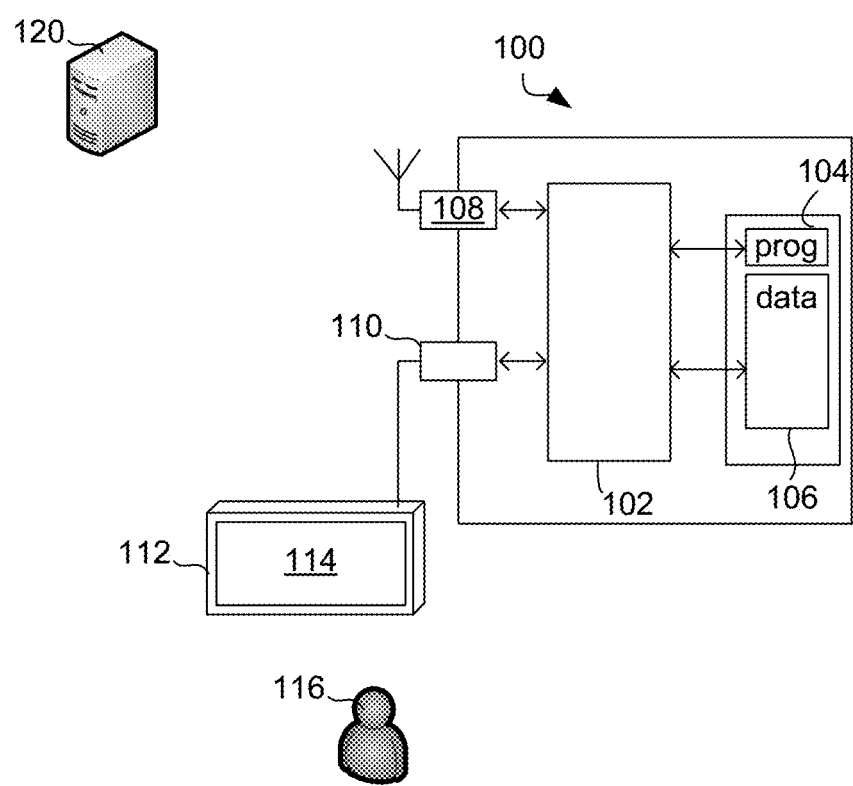
FIG. 1 illustrates a computer system for processing technical process data.

FIG. 1 illustrates a computer system 100 for processing technical process data. The computer system 100 comprises a processor 102 connected to a program memory 104, a data memory 106, a communication port 108 and a user port 110. The program memory 104 is a non-transitory computer readable medium, such as a hard drive, a solid state disk or CD-ROM. Software, that is, an executable program stored on program memory 104 causes the processor 102 to perform the method in FIG. 2, that is, processor 102 validates the process data, physically presents the process data in a bidding process, receives bidding data, selects one of multiple bids and stores an association between the biding data and the process data on data store 106.

The processor 102 may then store the process data on data store 106, such as on RAM or a processor register. Processor 102 may also send the physical representation of the process data via communication port 108 to a server, such as bidding platform host.

The processor 102 may receive data, such as process data, from data memory 106 as well as from the communications port 108 and the user port 110, which is connected to a display 112 that shows a visual representation 114 of the process data to a user 116. In one example, the processor 102 receives technical process data from an input computer system, such as a tablet computer, via communications port 108, such as by using a Wi-Fi network according to IEEE 802.11. The Wi-Fi network may be a decentralised ad-hoc network, such that no dedicated management infrastructure, such as a router, is required or a centralised network with a router or access point managing the network.

In one example, the processor 102 receives and processes the technical process data in real time. This means that the processor 102 validates and physically presents the technical process data in the bidding process every time technical process data is received from the input computer system and completes these steps before the input computer system sends the next technical process data update.

Although communications port 108 and user port 110 are shown as distinct entities, it is to be understood that any kind of data port may be used to receive data, such as a network connection, a memory interface, a pin of the chip package of processor 102, or logical ports, such as IP sockets or parameters of functions stored on program memory 104 and executed by processor 102. These parameters may be stored on data memory 106 and may be handled by-value or by-reference, that is, as a pointer, in the source code.

The processor 102 may receive data through all these interfaces, which includes memory access of volatile memory, such as cache or RAM, or non-volatile memory, such as an optical disk drive, hard disk drive, storage server or cloud storage. The computer system 100 may further be implemented within a cloud computing environment, such as a managed group of interconnected servers hosting a dynamic number of virtual machines.

It is to be understood that any receiving step may be preceded by the processor 102 determining or computing the data that is later received. For example, the processor 102 determines the technical process data and stores the technical process data in data memory 106, such as RAM or a processor register. The processor 102 then requests the data from the data memory 106, such as by providing a read signal together with a memory address. The data memory 106 provides the data as a voltage signal on a physical bit line and the processor 102 receives the technical process data via a memory interface.

It is to be understood that throughout this disclosure unless stated otherwise, nodes, edges, graphs, solutions, variables, associations, technical process data, bidding data and the like refer to data structures, which are physically stored on data memory 106 or processed by processor 102. Further, for the sake of brevity when reference is made to particular variable names, such as "technical impact" this is to be understood to refer to values of variables stored as physical data in computer system 100.

Figure 2:
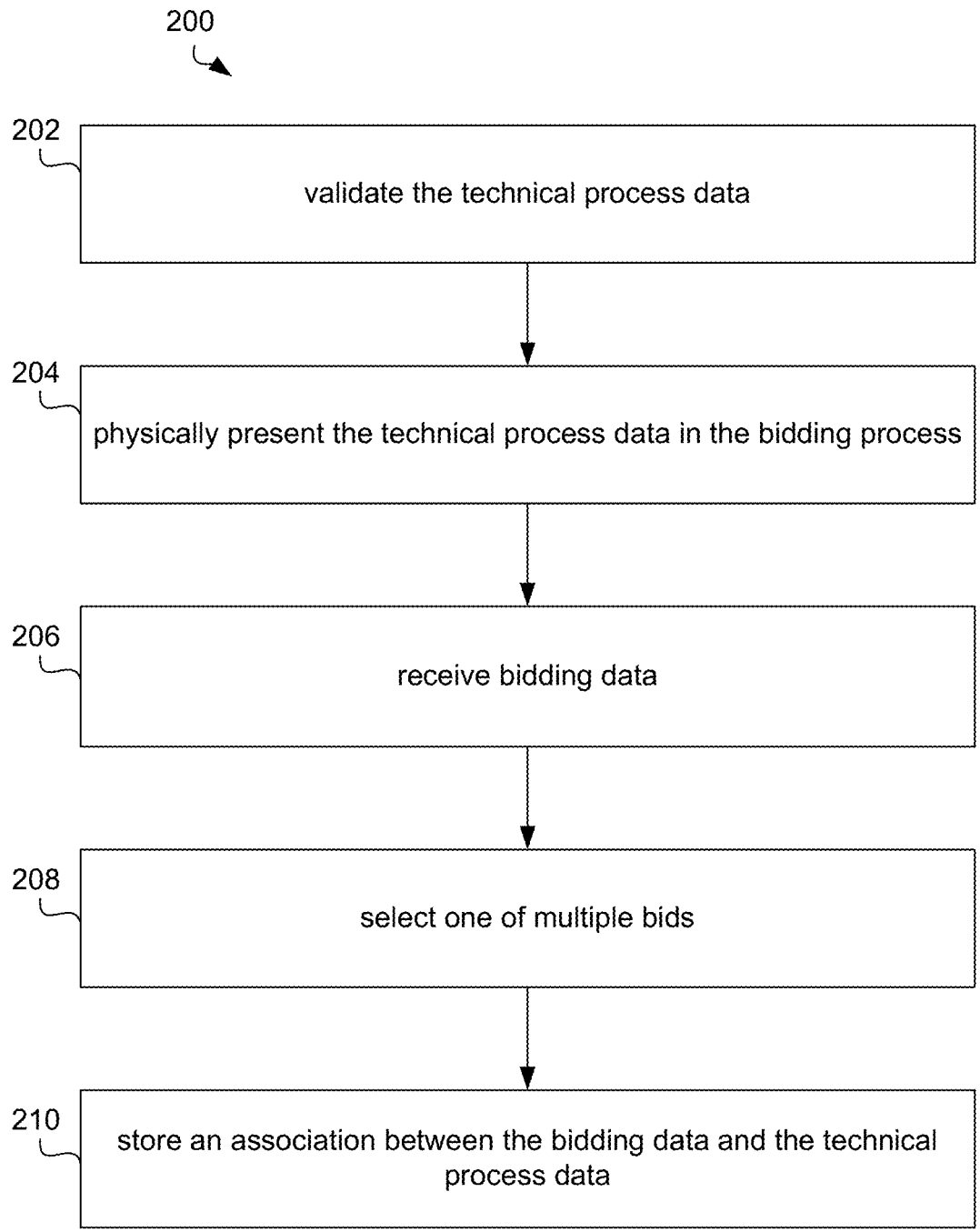
FIG. 2 illustrates a method for processing technical process data.

FIG. 2 illustrates a method 200 as performed by processor 102 for processing technical process data. FIG. 2 is to be understood as a blueprint for the software program and may be implemented step-by-step, such that each step in FIG. 2 is represented by a function in a programming language, such as C++ or Java. The resulting source code is then compiled and stored as computer executable instructions on program memory 104.

Figure 3:
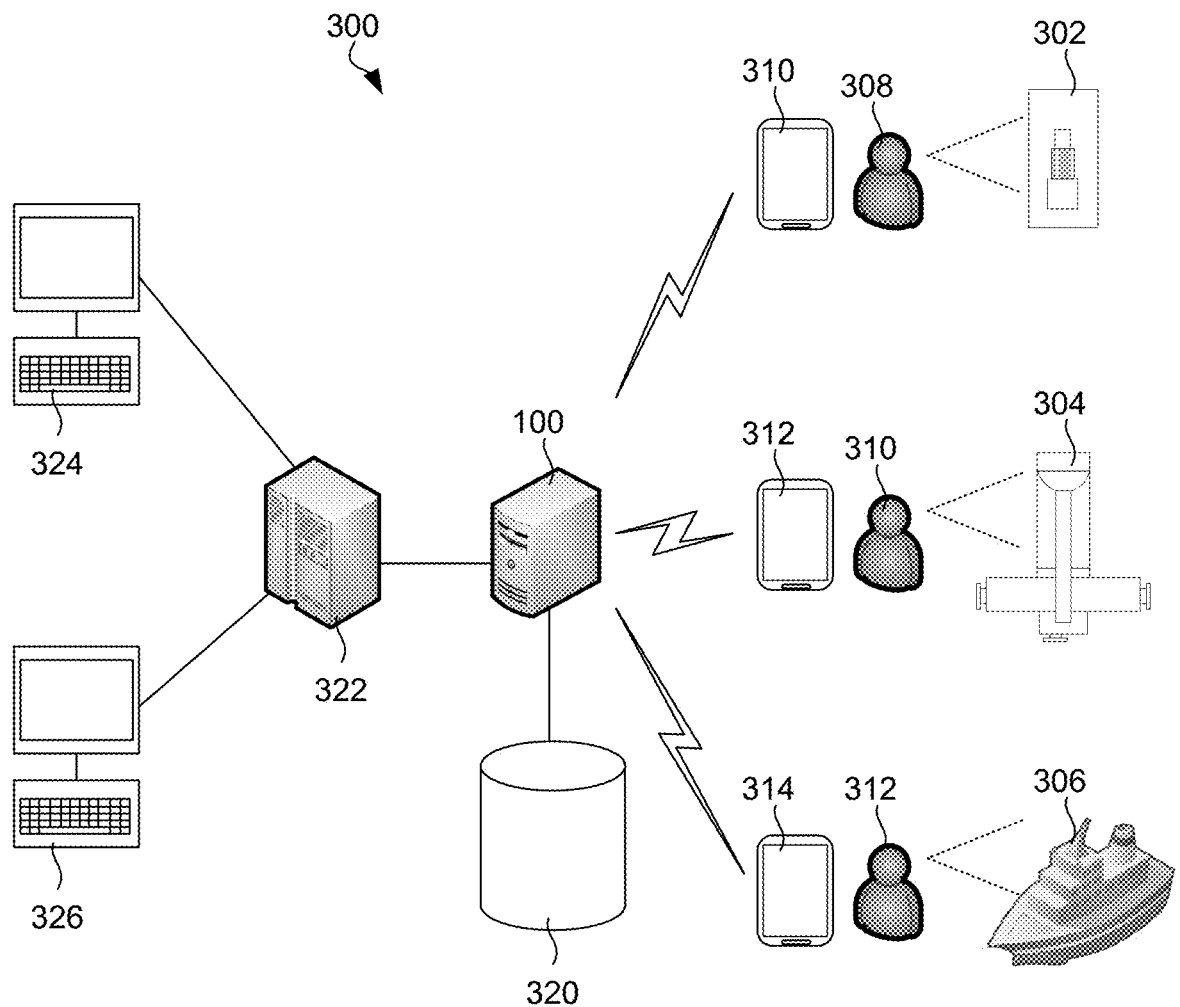
FIG. 3 illustrates a computer network in which the computer system of FIG. 1 may be integrated.

FIG. 3 illustrates a computer network 300 in which computer system 100 may be integrated. Computer network comprises multiple technical processes, including a generator 302, machinery, such as a vertical drill 304 and a diesel powered cargo ship 306 operating globally. The multiple technical processes 302, 304 and 306 may be subject to physical events. For example, a construction machine may sever the electrical connection between generator 302 and a hospital. As a result, the back-up power of the hospital is reduced, which means that a smaller number of operating theatres can be used at the same time. This reduces the overall number of patients that can be treated and reduces the overall revenue of the hospital. In other words, the technical impact of the physical event of a severed power line is a reduced number of available theatres, which can be represented ultimately by a monetary value.

This monetary value representing the technical impact may reflect the cost, that is, the loss of profit over one or more time periods after the physical event. For example, the monetary value for the first 3 hours, 3-8 hours, 24 hours, 48 hours, 72 hours and a total technical impact.

In the example of the vertical drill 304, storm damage may lead to water entering the vertical drill 304. Before the vertical drill 304 can resume operation, a technician will need to disassemble the drill, dry the inside and replace damaged components. The technical impact in this case is that the drill is not operational for the maintenance time period and again can be reflected by a monetary value over multiple different time periods as mentioned above.

In yet another example, diesel operated cargo ship 306 is subject to a physical event, such as adverse weather conditions, such as large swell, that damages the steering system. The technical impact in this case is that the cargo ship 306 is delayed, which may lead to a later delivery time and may even lead to reduced value of the cargo for time sensitive shipments, such as perishable food or price-volatile computer chips. Again, the technical impact may be represented by a monetary value as discussed above.

First technical expert 308 is responsible for generator 302, which means that first technical expert 308 is the best person to judge the technical impact of the physical event on generator 302. First technical expert 308 operates a mobile computer system 310.

Figure 4:
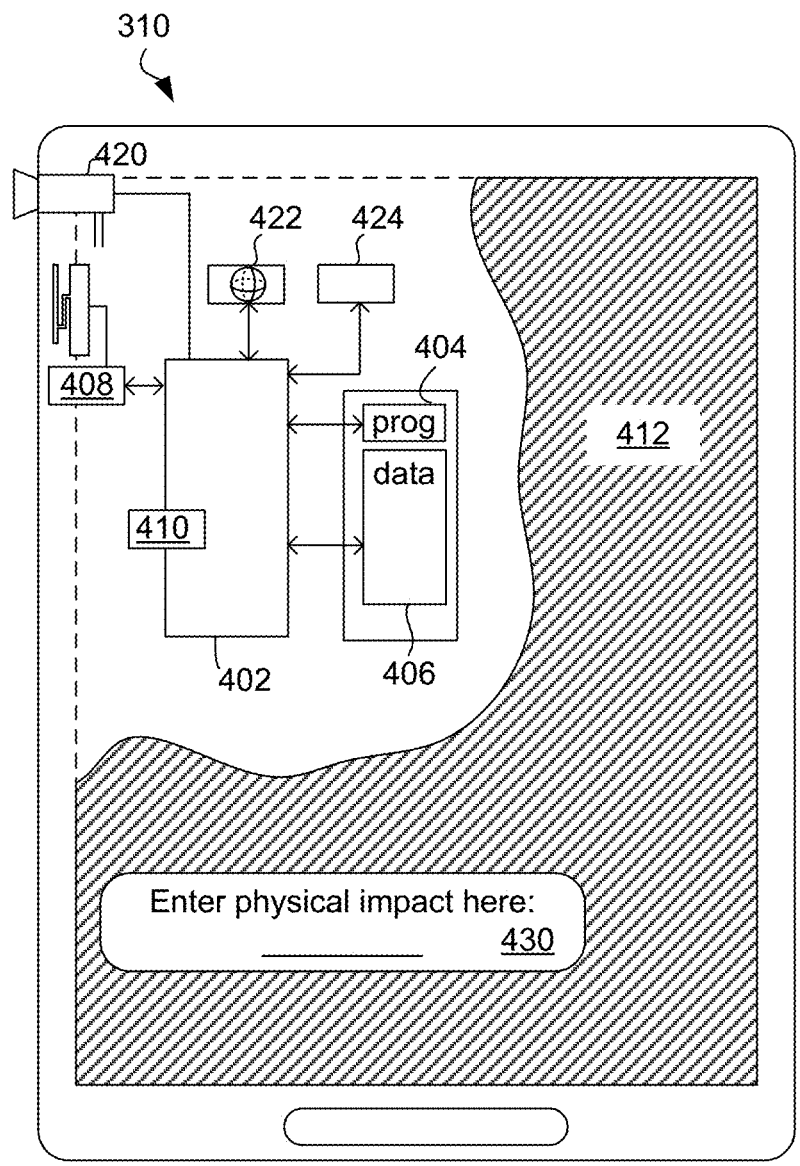
FIG. 4 illustrates mobile computer system for capturing technical process data in more detail.

FIG. 4 illustrates first mobile computer system 310 in more detail in the example of a tablet computer. In particular, first computer system 310 comprises a processor 402 connected to a program memory 404 and a data memory 306 to execute software and store data as described above with reference to FIG. 1. First mobile computer system 310 further comprises a communication port 408 connected to an antenna to wirelessly connect the first mobile computer system to a cellular network, such as 3G, 4G, LTE, Telemetry etc. or a Wifi network. Processor 402 is connected via a display port 410 to touch screen display 410. First mobile computer system 310 also comprises a camera 420, multiple inertial sensors 422 and a GPS location module 424, all of which generate sensor data and send the sensor data to processor 402. Touch screen 412 displays a user interface 430 to first technical expert 308.

As first technical expert 308 interacts with touch screen 412, touch screen 412 generates signals on an interrupt line that is connected to processor 402 via display port 410. The activation of the interrupt line causes the processor 402 to register input data from touch screen 412, such as pixel coordinates of the pixels where the first technical expert 308 touches the touch screen 412. Since processor 402 also generates the user interface 430, processor 402 can match the received pixel coordinates of user input against coordinates of functional elements of the user interface 430 to determine what data the first technical expert 308 enters.

In one example, the user interface 430 comprises an on-screen keyboard and the pixel coordinates of the first technical expert's 308 touches indicate numbers or letters. This way, the first technical expert 308 enters technical process data that relates to a technical impact of one or more physical events on a continuity of a technical operation, such as the operation of generator 302.

Generating a user interface may refer to processor 102 of computer system 100 generating HTML code, such as by dynamically adding information to previously generated HTML code and sending the HTML code to mobile computer systems 310, 312 and 314. In other examples, generating a user interface may refer to processor 402 rendering a user interface on screen 412 based on received HTML code. Other technologies in combination or instead of HTML code may equally be used, such as JavaScript, Java Applets, Flash, AJAX etc.

In the following example, the user interface 430 is a web interface that processor 402 renders based on HTML code received from computer system 100. Processor 402 then sends the technical process data to computer system 100 using a POST process or HMLHttp Request of an AJAX framework. In another example, software, such as a smartphone app is installed on program memory 404 through an app store, such as Google Play or ITunes. In this case, the app opens a TCP port and connects directly with computer system 100 to send the technical process data. For example, processor 402 sends the technical process data in the form of an encrypted XML data stream.

While first technical expert 308 enters technical process data in relation to generator 302, the second technical expert 310 enters technical process data into a second mobile computer system 312 in relation to the vertical drill 304. Similarly, third technical expert 312 enters technical process data into third mobile computer system 314. Second mobile computer system 312 and third mobile computer system 314 may comprise the components illustrated in FIG. 4. The three mobile computer systems 310, 312 and 314 may also be replaced by stationary personal computers or laptops or other computer devices, such a thin clients connected to computer system 100.

It will be appreciated that the three technical experts 308, 310 and 312 are dispersed over a wide area and potentially dispersed globally. As a result, without computer network 300, it would be difficult, if not impossible, to collect the technical process data from the technical experts 308, 310 and 312 in a time frame that allows meaningful processing. In other words computer network 300 is a dedicated network for processing technical process data and therefore, the hardware and software involved in computer network 300 are significant parts of the proposed solution and are significantly more than the mere entering of data by multiple users.

Figures 5, 6:
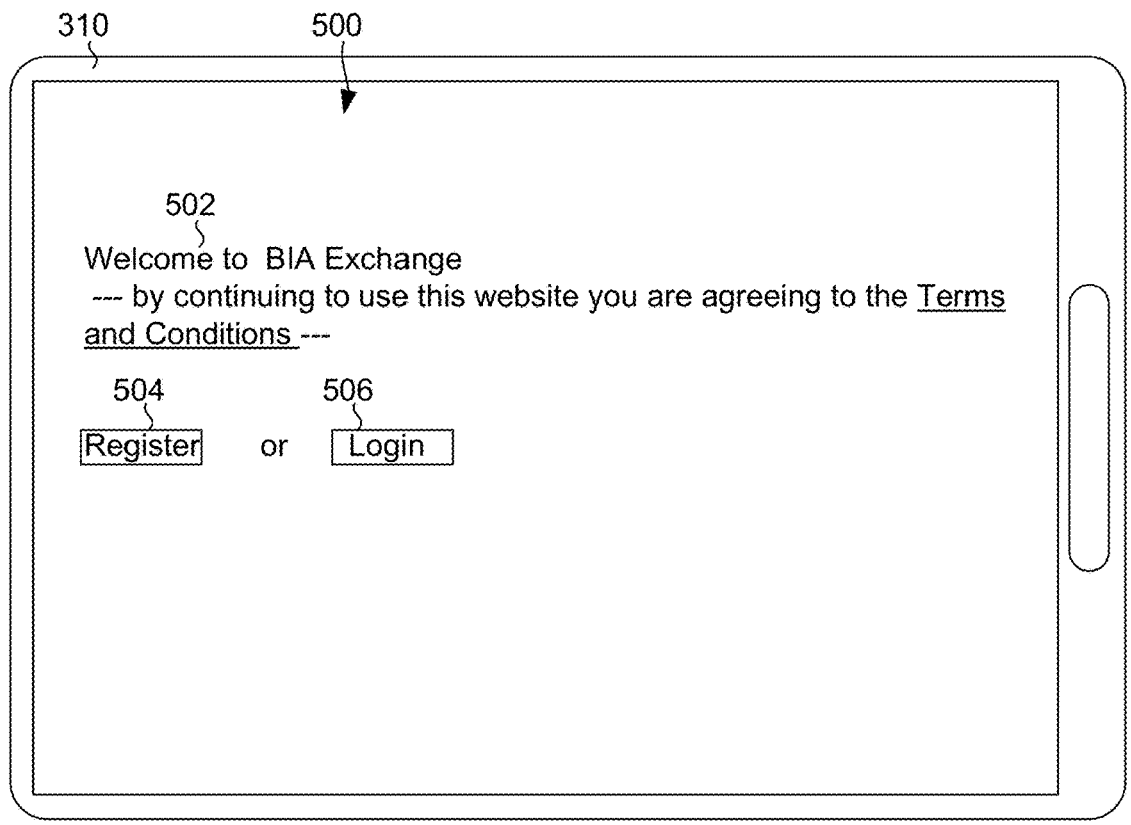
FIG. 5 illustrates a user interface to welcome a technical expert.
FIG. 6 illustrates a user interface to register the technical expert.

FIG. 5 illustrates a first user interface 500 displayed on first mobile computer system 310. The first user interface 500 comprises a welcome message, a first user control element 504 to allow first technical expert 308 to register and a second user control element 506 to allow the first technical expert 308 to login with previously registered user credentials.

FIG. 6 illustrates a second user interface 600 that allows the first technical expert 308 to register. This registration interface 600 comprises user input fields for:
- name 602 of the first technical expert 308;
- for BCI/DRI certification/membership number 604;
- Industry description 606;
- NACE Code 608;
- Geographical Area 612;
- Whether the organisation possesses a full BCM Plan that is regularly updated and tested 614;

If YES, how often the BCM plan is updated (Monthly/
Quarterly/Semi-Annually) 616,
Whether first technical expert 308 had any significant
incidents/claims during the last six years 618
Preferred Password 620 (must contain at least 8 alphanumerics and include at least one interpunction mark); and
Approving Director 622 (any change in approving authority must be advised immediately).

User interface 600 further comprises a submit user control element 624. Once processor 302 detects user interaction in relation to the submit user control element 624, that is, processor 302 detects that the user has pressed the submit button 624, processor 302 sends the entered data to computer system 100, where the profile data is stored.

When first technical expert 308 returns to user interface 500 and selects the login control 502, processor 402 generates a user interface to allow the first technical expert 308 to provide a user name and password. Processor 402 then sends the provided user name and password to computer system 100 for validation. If the username and password correspond to an existing account, computer system 100 sends the data that was previously entered into user interface 600 to processor 402.

FIG. 7 illustrates a third user interface 700 that processor 302 generates upon successful registration and login. In this example, the third user interface 700 follows a grid layout with multiple rows. User interface 700 comprises respective rows for:
Critical function 702,
Impact within 3 hrs 704,
Impact within 3 hrs-8 hrs 706
Impact within 24 hrs 708
Impact within 48 hrs 710
Impact within 72 hrs 712
Total Impact in $ 714, and
Percentage of Impact comparing to Company-wide impact 716.

Third user interface 700 further comprises an observations input field 718 allowing the first technical expert 308 to enter observations.

In order to interact with user interface 700 first technical expert 308 can click or tap on any of the empty grid cells to activate that grid cell for data input. Processor 402 detects this interaction and correlates the coordinates of the user interaction with the coordinates of the generated user interface 700 to activate an input field. As the first technical expert 208 enters the data into the activated user input field, processor 402 receives this data, stores the data locally on data store 406 and sends the entered data to computer system 100.

FIG. 8 illustrates user interface 700 after first technical expert 308 has entered the relevant data including observations into text box 718 in FIG. 7.

In one example, the data structures illustrated in FIGS. 7 and 8 comprise a further column for important notes and descriptions, such as "Supply chain issue" or "Power outage" for impact categories #1 and #2, respectively.

In this example, computer system 100 receives from first technical expert 308 three impact categories and a reputational impact of a physical event related to generator 302 on the continuity of the technical operation. Similarly, computer system 100 receives from second technical expert 310 and third technical expert 312 further technical process data relating to the technical impact of physical events in relation to the vertical drill 304 and cargo ship 306, respectively.

FIG. 9 illustrates a further user interface 900 in an example where the user interface 900 is customised to the first technical expert 308. In this example, the technical operation of the entire network shown in FIG. 3 is segmented into three segments. Each of the three segments is associated with a respective one of the technical experts 308, 310 and 312. Computer system 100 stores an association between segments of the technical operation and technical experts on data store 106. This way, computer system 100 can generate a different user interface for each technical expert, such that each technical expert can only provide technical process data for the segment of the technical operation associated with that expert.

In the example of FIG. 9, the user interface 900 comprises a prominent heading 902 to indicate to the first technical expert 308 that the user interface is applicable for technical process data related to generator 302. In addition to the heading 902 some of the cells may be pre-populated or deactivated depending on the segment of the technical operation. For example, some critical functions are assigned to a particular segment of the technical operation and as a result, the names of these critical functions are pre-populated for the technical expert associated with that segment. This way, the technical operation can be structured and the technical process data can be received by computer system 100 in a well-organised manner. Further, it is more convenient, less error-prone and more efficient for the technical experts to enter the technical process data.

Returning back to FIG. 2, processor 102 receives the technical process data through input port 108 from the multiple technical process experts 308, 310 and 312. As explained above, the technical process data relates to a technical impact of one or more physical events on a continuity of a technical operation.

Processor 102 then validates 202 the technical process data. For example, processor 102 checks that all fields hold data, that is, there is no empty fields and detects typos, such as formatting errors of monetary values and unrealistic values.

In examples where processor 102 receives the technical process data from multiple technical process experts separately, that is, in separate data structures, processor 102 may consolidate the data into a single data structure, such as in the form of records into a single SQL database 320. In one example, processor 102 stores each row in FIG. 8 as a record in database 320. In cases where database 320 holds technical process data associated with multiple independent technical operations, such as different companies, the database 320 may comprise a data field for a technical operation identifier such that processor 102 can retrieve records that belong to the same technical operation from the database 320.

In one example database 320 contains the categories and fields as shown in FIG. 8 and in addition may include "approval fields" and data-verification/cross-reference checks to enable data-mining for later bundling and serve as an alternative origination channel for the Insurance Linked Securities (ILS).

Likewise, database 320 may possess a static and dynamic option: For very short term insurance coverage (or for specific purposes) static option may be suitable; however for any extended period of time (i.e. more than 30 or 60 days) the collected data may be fed on dynamic basis. This way the technical process data can be maintained on a regular basis to represent a cornerstone of a well-prepared Business Continuity Management Plan.

The dynamic feature may be enabled through various communication channels and knowledge transfers that may not be limited to:
Permanent internet or Telephone connection;
Telemetry services;
Artificial Intelligence
Machine Learning
Machine-to-Machine
Short burst radio-waves that may transmit "updates" on a regular intervals during the day; and
SMS/Text message reminders sent to Management (or authorised personnel) to provide manual update (or confirm data validity).

The communication channel may further involve a crypto-currency (bitcoin type) data verification that also serves as an enabler of further transfer of risk and costs of recovery associated with the particular operation or an entire business. This feature makes these risk exposures and their values/pricings "crypto-currency ready" so it can fit any current or future exchange or new instruments such as ILS or similar.

In some examples, processor 102 performs methods based on Bitcoin, Ethereum and other distributed ledger technologies to manage contracts, trade and trust—from decentralised exchanges and proof of ownership registers, to self-executing contracts and micro payments related to the technical impact data. Processor 102 may host a blockchain-based virtual machine that securely records and incentivises the validation of transactions, i.e. code executions, made through a cryptocurrency. Contracts may be written in Solidity, Serpent or LLL. They may be compiled by processor 102 into bytecode before being deployed to the blockchain. Processor 102 may be communicatively coupled to servers of HitFin, Inc., 55 E 3rd Ave, San Mateo, CA 94401, or Symbiont.io ledger and clearing exchange based in the United States, to facilitate the settlement of contracts or contracts for derivatives. It is noted, however, that the proposed solution provides the technical tools to maintain a link between the traded risk and the underlying technical process data from the technical experts.

One challenge in implementing such contracts is that they may require reference to an external price ticker; for example, a desirable application may a smart contract that hedges against the volatility of ether or another cryptocurrency with respect to the price of the derivative in US dollar that is determined by the technical process data. This may require the contract to know what the value of ETH/USD is. One way to do this is through a "data feed" contract maintained by a specific party (eg. the computer system 100 in FIG. 1) designed so that processor 102 has the ability to update the contract as needed, and providing an interface that allows other contracts to send a message to that contract and get back a response that provides the price.

Given that critical ingredient, the hedging contract may look as follows:
Wait for party A to input 1000 ether.
Wait for party B to input 1000 ether.
Record the USD value of 1000 ether, calculated by querying the data feed contract, in storage, say this is $x.
After 30 days, allow A or B to "reactivate" the contract in order to send $x worth of ether (calculated by querying the data feed contract again to get the new price) to A and the rest to B.

Such a contract would have significant potential in crypto-commerce. One of the main problems cited about cryptocurrency is the fact that it's volatile; although many users and merchants may want the security and convenience of dealing with cryptographic assets, they many not wish to face that prospect of losing 23% of the value of their funds in a single day. Here, instead of a single issuer providing the funds to back up an asset, a decentralized market of speculators, betting that the price of a cryptographic reference asset (eg. ETH) will go up, plays that role. Unlike issuers, speculators have no option to default on their side of the bargain because the hedging contract holds their funds in escrow. Note that this approach of physically presenting the technical process data in the bidding process in step 204 in FIG. 2 is not fully decentralized, because a trusted source 100 is still used to provide the price ticker. This is a significant improvement in terms of reducing infrastructure requirements and reducing the potential for fraud.

After evaluating the technical process data processor 102 initiates a bidding process. This may comprise packaging the data and transferring the data to a bidding platform. Initiating the bidding process may also comprise generating metadata about the technical process data that can be used as descriptors in the bidding process. For example, processor 102 may extract the company name and a type of technical operation to be used as searchable keywords.

Referring back to FIGS. 1, 2 and 3, processor 102 physically presents 204 the technical process data in the bidding process. In one example, physically presenting the technical process data in the bidding process comprises sending the validated technical process data to a bidding server 322. However, the bidding process may equally be hosted by computer system 100.

Bidding server 322 comprises similar components as described for computer system 100 with reference to FIG. 1. Therefore, when reference is made to processor 102 this may refer to the processor of bidding server 322 or the processor of computer system 100.

Connected to bidding server 322 is a first bidding client computer system 324 and a second bidding client computer system 326. Processor 102 generates user interfaces that can be accessed by the bidding client computer systems 324 and 326 to allow placing bids for technical operations.

Figures 10, 11:
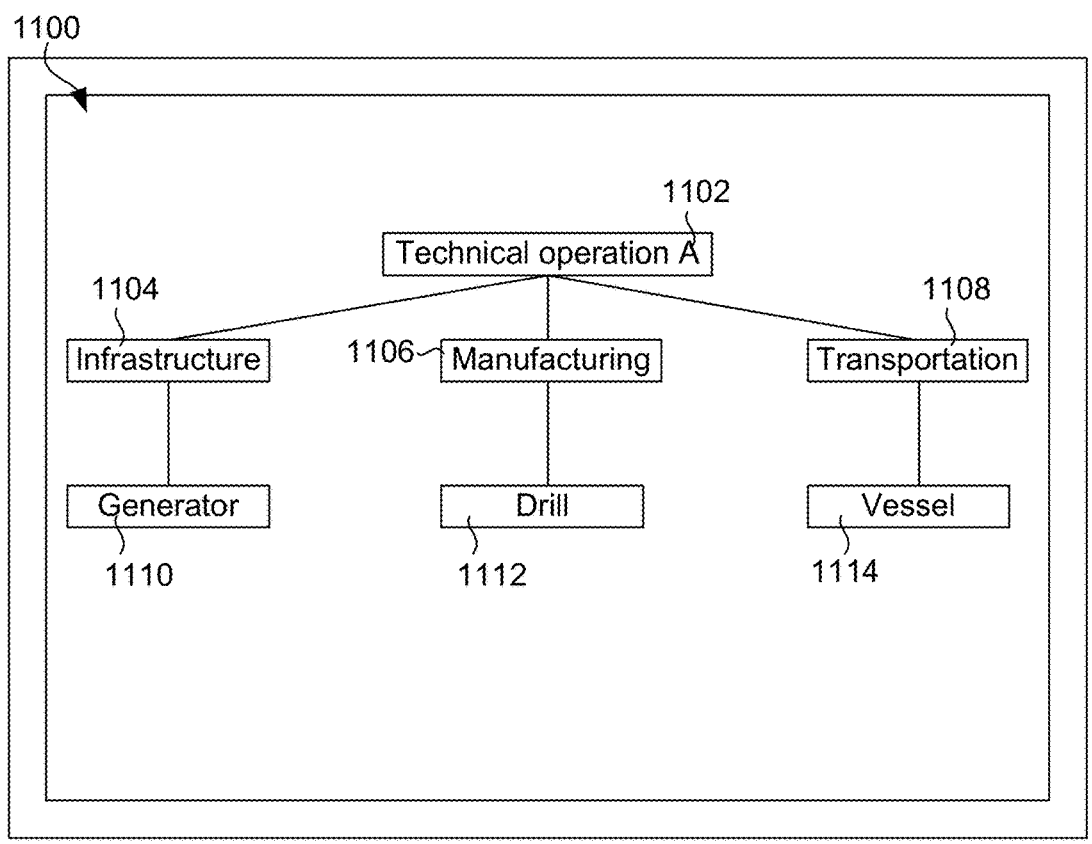
FIG. 10 illustrates a user interface that physical presents technical process data in a bidding process.
FIG. 11 illustrates a user interface for reviewing technical process data.

FIG. 10 illustrates a user interface 1000 that physical presents the technical process data in the bidding process. In this example, physically presenting the technical process data comprises displaying an aggregate value, such as the total impact value associated with each of multiple technical operations. In the example of FIG. 10, the bidding process comprises three different technical operations 1002, 1004 and 1006. Associated with each of the technical operations 1002, 1004 and 1006 are respective total impact values 1008, 1010 and 1012. Further associated with each of the technical operations 1002, 1004 and 1006 are respective current bid values 1014, 1016 and 1018.

A finance specialist, such as an insurance manager can see the available technical operations and their respective impact values and can determine whether he can place a better bid. In one example, the bidding process is a reverse auction where the bidding starts at an unrealistically high price and any further bids need to be less than the current bid. This way, the insurance manager can decide whether his insurance provider can offer an insurance based on the technical process data for a lower premium. In one example, the current bid reflects the monthly premium.

The finance specialist can select one of the technical operations, such as technical operation A to review more details about technical operation A.

FIG. 11 illustrates a user interface 1100 for reviewing technical process data. In this example, processor 102 generates the user interface 1100 in a hierarchical manner to represent the different segments in technical operation 1002. In this example, user interface 1100 comprises a root node 1102 for technical operation A and three segment nodes for 'Infrastructure' 1104, 'Manufacturing' 1106 and 'Transportation' 1108 representing the three segments of the technical operation.

'Infrastructure' segment 1104 is further associated with 'Generator' node 1110 relating to generator 302 in FIG. 3. 'Manufacturing' segment 1106 is further associated with 'Drill' node 1112 relating to vertical drill 304 in FIG. 3. 'Transportation' segment 1108 is further associated with 'Vessel' node 1114 relating to diesel powered cargo ship 306 in FIG. 3.

In another example, processor 102 generates a user interface (not shown) that displays the technical process data in a grid layout as illustrated in FIG. 8.

With existing insurance services the risk and therefore the insurance premium is calculated by actuaries based on abstract values because computer technology was not available that allows more concrete calculations. In contrast, this disclosure provides a physical computer implementation that allows the calculation of insurance premiums based on technical process data instead of abstract estimates. In other words, the disclosed solution transforms the process of determining insurance premium into a concrete, tangible and technical system that processes technical process data and that is tightly integrated into the technical operations. This integration occurs at the computer architectural level since the mobile computer system 310, 312 and 314 are provided to the technical experts that monitor the technical operation.

The financial manager using first bidding client computer system 324 can click on the current bid in order to enter a new bid value for a new bid. Bidding client computer system 324 generates bid data including the new bid value and may generate a unique bidID for this new bid. Processor 102 receives 206 this bidding data from bidding client computer system 324 associated with this bid through the unique bidID. The bidding data may be in the form of XML data or HTML POST values.

Similarly, processor 102 receives a bid from second bidding client computer system 326. This process may be repeated until the current bid settles and one of the two financial managers stops entering new bids. Processor 102 then selects 208 one of multiple bids based on the bidding data. In one example, processor 102 selects the bid with the lowest bidding value.

After the selection of the bid, processor 102 stores 210 an association between the bidding data associated with the selected one of the multiple bids and the technical process data on the database 320.

Figures 12, 13:
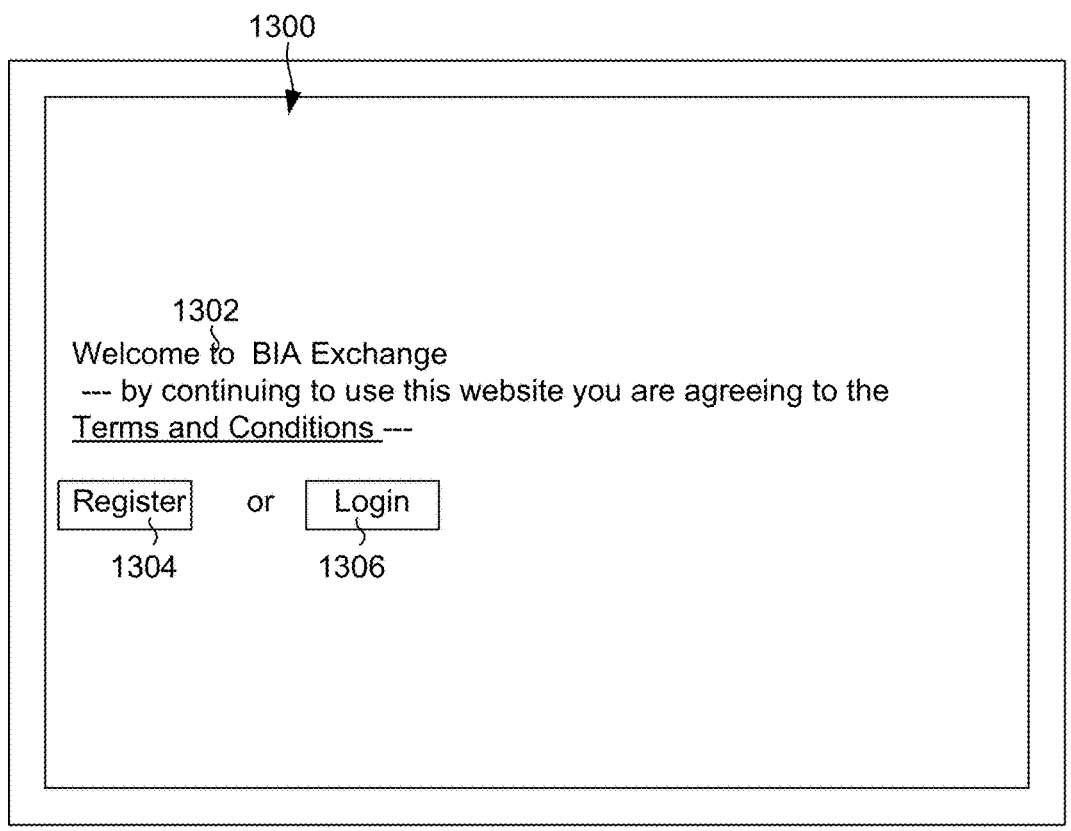
FIG. 12 illustrates an aggregated view of multiple technical operations.
FIG. 13 illustrates a welcome user interface for a financial manager.

FIG. 12 illustrates an aggregated view of multiple technical operations. For example, a reinsurance company may have won bids on a large number of technical operations and is exposed to a large number of risks based on the impact of various different physical events on the technical operations. Since the technical process data is available, processor 102 can aggregate quantify the risk across the entire reinsurance portfolio as shown in FIG. 12. This is enabled by the computer systems disclosed herein and in particular, computer system 100.

Another advantage of the proposed systems and methods is that the technical experts can update the technical process data and the physical display in the bidding process can be updated in real-time. This allows a real-time assessment of the technical process data and the bidding process may operate continuously, such that the bidder with the lowest current bid ears the premium and holds the risk until a lower bid is entered based on updated technical process data.

FIG. 13 illustrates a bidder user interface 1300 comprising a welcome message 1302 and user control elements 1304 and 1306 for registration and login, respectively. When the financial manager activates the registration control element 1304, processor 102 generates registration user interface 1400 shown in FIG. 14.

Registration user interface 1400 comprises user input fields for selecting insurance or reinsurance 1402, for selecting industries of interest 1404, geographic exposure 1406 and a password 1408. Some inputs may comprise drop down menus or other single or multiple selection fields. Processor 102 receives the entered data and performs a filtering operation to display only those technical operations that meet the entered criteria in FIG. 10.

This way insurance company may further be able to view and appropriately select clients according to the insurance company's risk-appetite and internal company strategy. They will be able to filter clients and type of exposure by applying various Industry and/or Geographical criteria (similar to any other B2B, such as CarSales and eBay for instance).

FIG. 15 illustrates a sample report 1500 as physically generated by processor 102 in the form of a HTML coded web-page or pdf document, for example.

Clicking on client's name triggers processor 102 to generate a display of further details. Based on insurance company risk appetite and other individual criteria, the financial managers of the insurance will be able to place an appropriate bid.

It will be appreciated by persons skilled in the art that numerous variations and/or modifications may be made to the specific embodiments without departing from the scope as defined in the claims.

It should be understood that the techniques of the present disclosure might be implemented using a variety of technologies. For example, the methods described herein may be implemented by a series of computer executable instructions residing on a suitable computer readable medium. Suitable computer readable media may include volatile (e.g. RAM) and/or non-volatile (e.g. ROM, disk) memory, carrier waves and transmission media. Exemplary carrier waves may take the form of electrical, electromagnetic or optical signals conveying digital data steams along a local network or a publically accessible network such as the internet.

It should also be understood that, unless specifically stated otherwise as apparent from the following discussion, it is appreciated that throughout the description, discussions utilizing terms such as "estimating" or "processing" or "computing" or "calculating", "optimizing" or "determining" or "displaying" or "maximising" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices.

It should further be understood that the technical process data may be in any suitable format, such as according to ISO 22317 or more particularly ISO 22317:2015, which is incorporated herein by reference. In other words, the technical process data may relate to data from a business impact analysis (BIA). In this example, the user interface 900 for entering technical process data is technically implemented to cover the categories in ISO 22317:2015/2016. Further, the validation step 202 in FIG. 2 may relate to validating the technical process data against this standard. This may include checking that all required data fields were entered. The above methods and systems may especially be applicable to insurance linked securities (ILS), sidecars, Industry Loss Warrants (ILW) and more particularly to catastrophe bonds (CAT bonds) and derivatives where risk and impact are calculated for investment purposes. In those applications, computer network 300 in FIG. 3 may comprise a trading system of derivatives or may be electrically connected to a derivatives trading system.

In further examples, other professional membership organisations may use ISO22317 (BIA) ISO22318 (BIA in supply chain) or a partial "Impact Analysis" that is suitable for the specific industry or a market niche. Therefore, the systems and methods herein may use data curated by the Investment Management Due Diligence Association (https://imdda.org) is used in a wide range of services, M&A, JV etc. Aforementioned ISO standards may be adopted and independent certification obtained through the training and certification body such as TuV, SGS, BSI and similar. Parallel organisation to the BCI and DRII may provide data or data schemes to the disclosed systems and methods given that these activities may become a part of the wider due diligence undertaking. This may avoid the need to hire BCI/DRII external resources, which may reduce the overall ISO compliance cost.

IoT information, Predictive Maintenance/Predictive Analytics, Machine Learning and raw data may be supplied to the disclosed methods and systems. Therefore, Australian, US and other engineering associations around the world i.e.: http://www.aaes.org/ or other scientific bodies or organisations can follow the same suit as aforementioned IMDDA using the disclosed systems and methods.

Processor 102 can use the technical process data to manage a wide spectrum of financial products, but also for other industries by performing computer implemented methods of estimation, forecasting or specific research. Processor 102 may bundle data through Insurance Linked Securities (ILS) or other instruments that could be used for primary or secondary trading, evaluation or establishing financial derivatives (futures, options/warrants, swaps).

Insurance, Re-Insurance Companies, Governments, or any Scientific, Philanthropic or other entity with authorised access can provide search criteria to processor 102 and processor 102 provides quality information and segregates under preferred criteria, such as tiering (i.e. low, medium or high) level of exposure (for instance interrogating top 20% of transaction—client exposures with maximum impact; or examining specific geographical territory, particular industry (i.e. electric power generation plants, hospitals facing pandemic threat consequences within specific state, or entire country).

The BIA may be a part of the Business Continuity Management and Planning science and assessment. BIA may also be a part of other assessments and other Quality Standards. One example is ISO9001:2016 and or any of its updated editions. In one example, processor 102 determines whether the technical impact data has approval of top management, such as by maintaining a database of top management personnel and corresponding signatures and checking the entered data against that database. This means that processor 102 generates an alert if the management does not accept the level of risk, which provides a formal signoff.

As mentioned earlier, there are two types of information that can be submitted to the BIAX:

Static snapshot of current exposure of the company, such could have only limited value to the "Interested Party" (Insurance or Re-Insurance Company) given that it covers very short period of time. These static evaluations may be performed by risk assessment tools installed as software on program memory 104.

Dynamic evaluation or monitoring is a main advantage of the proposed methods and systems which brings to interested parties (Insurance companies, governments, research organisations and other) a dynamic perspective and looks at future requirements, supply chain and resources necessary for operation and any post-incident swift recovery.

This may include monitoring and passing on the information to the disclosed system of FIG. 1. These data updates generated by any device, such as sensors, Internet-of-Things (IoT) transmitters, Artificial Intelligence, Machine-to-Machine (M2M) and other means that can be used for maintenance, predictive maintenance of particular resources in location A, B or C (i.e. city); or particular monopolistic supplier. If any of these changes affect the impact to the continuity of the technical process, then it impacts the underwriting contract; or acceptable or agreed cover of insurance.

The proposed solution addresses risks and transfer (packaging) of that risk regardless of its origin and irrespective of communication means where this information is used for the insurance, re-insurance or pricing purposes.

Technical process data originated by each entity may be transmitted to the Central Database (B2B platform) using third party software; however these may be verified and approved by the technical team. This ensures data integrity. Such software may enable continuous, uninterrupted data feed and monitoring of company (subject) exposure and its capacity to recover swiftly. As a result, insurance industry can adjust its pricing on-the-go. Dynamic feature provides a more objective assessment than actuary calculation, which results in a Win-Win situation. Less risk, better flexibility and ultimately better pricing for all parties involved.

Each data-block (in a static option) or continuous data-feed in dynamic option may be clearly distinguished through a Unique Customer Identification that may also contain crypto-currency features to enable seamless transition for securitisation and trading purposes.

In one example, computer system 100 in FIG. 1 operates as an issuing authority (interchange) for other products and instruments that may be traded through a Blockchain or any other platform. So other parties can use it for their own Exchanges/Platforms. If the Verisign is the authority for "origin" authentication, computer system 100 may operate in a similar way for valuation based on principles related to technical process data. Computer system 100 may provide a verification of BCM professionals and confirm approval of the most senior management.

There are numerous valid reasons why this initiative could make sense:

Firstly, there is no proper evaluation for many products currently being traded on the markets and even if there is, these are extremely complex models that even traders do not completely understand.

Likewise, some of the instruments and its derivatives have gone so far that the seller, let alone a buyer could properly trace underlying security which is supposed to represent.

Having the proposed assessment of technical process data provides additional attributes that makes the product (or a trade) more transparent.

In one example, the technical process data includes, follows, adhere or refers to holistic principles of the Balanced Scorecard encompassing Financial impacts or results, Employee and Customer impact, Societal Impact; impact on Internal Processes, measures (including matrix, formulas and algorithms) causes, effects, leading and lagging indicators that may be also linked to the continuity of the business, its reputation, potential losses, executive remuneration or overall compensation system of the firm or organisation.

In a further example, validating the technical process data comprises validating the technical process data against ISO or other quality or an industry standard, but particularly ISO22301 Societal Security, ISO22317 Business Impact Analysis, ISO22318 Business Impact Analysis in Supply Chain, ISO31000 Enterprise Risk, ISO27001 Cyber Security and most recently issued ISO9001:2015, ISO9001:2016 for Quality and any of its most recent updates that may apply in future, which emphasise Risk Management and Business Continuity processes and establishes key responsibilities of a Senior and Executive Management.

In yet a further example, the processor is further configured to operate a Blockchain, security certificates or a customised cyber security and/or technical solution or a ledger to facilitate distributed communication to the multiple bidding client computer systems.

The present embodiments are, to be considered in all respects as illustrative and not restrictive. It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A computer system for processing technical process data, the computer system comprising:
   an input port to receive technical process data from multiple technical process experts on a dynamic basis, wherein the technical process data relates to a technical impact of one or more physical events on a continuity of multiple technical operations;
   a database to store the technical process data;
   a processor configured to:
   validate the technical process data against a business impact analysis standard;
   determine an aggregate value of the multiple technical operations based on the technical process data;
   calculate an insurance premium based on the technical process data;
   bundle the technical process data through one or more instruments or financial derivatives for primary or secondary trading of a traded risk;
   receive a continuous feed of updates of the technical process data from one or more sensors that monitor the technical operation;
   dynamically evaluate and monitor the technical process data to maintain the technical process data on a regular basis through one or more communication channels, wherein the processing of the technical process data maintains a link between the traded risk and the technical process data received from the one or more sensors that monitor the technical operation and update the technical process data in real-time; and
   update an underwriting contract or cover of insurance to transfer the traded risk in the multiple technical operations,
   wherein:
   the underwriting contract or cover of insurance comprises a self-executing contract,
   the processor is further configured to validate transactions based on the technical process data updated in real time to facilitate the settlement of the self-executing contract and to reflect the impact of changes to the continuity of the multiple technical operations, and
   the self-executing contract provides an interface that allows other contracts to send a message to that contract and get back a response that provides the insurance premium based on the technical process data updated in real time.

2. The computer system of claim 1, wherein the input port is connected to multiple client computer systems, each of the multiple client computer systems comprising:
   a processor to generate a user interface for receiving technical process data that relates to a technical impact of one or more physical events on a continuity of a technical operation;
   a data port to send the technical process data to the computer system according to claim 1.

3. The computer system of claim 1, wherein the processor is configured to generate a user interface that allows one of the multiple technical process experts to enter technical process data, wherein the user interface is specific to that one of the multiple technical process experts.

4. The computer system of claim 1, wherein the technical process data relates to a business continuity analysis or a business impact analysis.

5. The computer system of claim 1, wherein validating the technical process data comprises validating the technical process data against ISO 22317.

6. The computer system of claim 1, wherein validating the technical process data comprises validating the technical process data against ISO/TS 22317 of 2015 or later and/or ISO22318 of 2015 or later.

7. The computer system of claim 1, wherein the processor is further configured to determine an aggregate value of multiple technical operations based on the respective technical process data.

8. The computer system of claim 1, wherein the processor is further configured to physically present the technical process data, wherein the step of physically presenting the technical process data comprises generating a user interface comprising input elements to filter a subset of multiple technical operations.

9. The computer system of claim 1, wherein the computer system is a bidding server, and wherein the processor is further configured to:
   initiate a bidding process;
   physically present the technical process data in the bidding process;
   receive bidding data from multiple bidding client computer systems associated with multiple bids;
   select one of multiple bids based on the bidding data; and
   store an association between the bidding data associated with the one of the multiple bids and the technical process data on the database.

10. The computer system of claim 1, wherein the processor is further configured to operate a Blockchain to facilitate distributed communication to the multiple bidding client computer systems.

11. The computer system of claim 1, wherein the processor is further configured to verify the technical process experts.

12. A computer implemented method for processing and distributing technical process data, the method comprising:
- receiving the technical process data from multiple technical process experts on a dynamic basis, wherein the technical process data relates to a technical impact of one or more physical events on a continuity of multiple technical operations;
- storing the technical process data on a database;
- validating the technical process data against a business impact analysis standard;
- consolidate the technical process data into the database;
- determining an aggregate value of the multiple technical operations based on the technical process data;
- calculating an insurance premium based on the technical process data;
- bundling the technical process data through one or more instruments or financial derivatives for primary or secondary trading of a traded risk;
- receiving a continuous feed of updates of the technical process data from one or more sensors that monitor the technical operation;
- dynamically evaluating and monitoring the technical process data to maintain the technical process data on a regular basis through one or more communication channels, wherein the processing of the technical process data maintains a link between the traded risk and the technical process data received from monitoring devices that monitor the technical operation and update the technical process data in real-time; and
- updating an underwriting contract or cover of insurance to transfer the traded risk in the multiple technical operations, wherein:
- the underwriting contract or cover of insurance comprises a self-executing contract,
- the method further comprises validating transactions based on the technical process data updated in real time to facilitate the settlement of the self-executing contract and to reflect the impact of changes to the continuity of the multiple technical operations, and
- the self-executing contract provides an interface that allows other contracts to send a message to that contract and get back a response that provides the insurance premium based on the technical process data updated in real time.

13. A non-transitory computer readable medium with program code stored thereon that, when executed by a computer, causes the computer to perform the method of claim 12.

14. A computer network for processing technical process data, the computer network comprising:
- a computer system according to claim 1;
- multiple client computer systems, each comprising:
  - a processor to generate a user interface for receiving technical process data that relates to a technical impact of one or more physical events on a continuity of a technical operation;
  - a data port to send the technical process data to the computer system according to claim 1.

15. The computer network of claim 14, wherein the processor of each of the multiple client computer systems is configured to operate a blockchain for sending the technical process data.

16. The computer system of claim 1, wherein the processor is further configured to:
- validate the technical process data and initiate a bidding process,
- physically present the technical process data in the bidding process,
- receive bidding data from multiple bidding client computer systems associated with multiple bids,
- select one of multiple bids based on the bidding data, and
- store an association between the bidding data associated with the one of the multiple bids and the technical process data on the database.

17. The computer system of claim 1, wherein the one or more communication channels involve a crypto-currency data verification to provide transfer of the traded risk and costs of recovery associated with the technical operation.

18. The computer system of claim 17, wherein each of multiple data-blocks in the continuous data feed is distinguished through a Unique Customer Identification that contains crypto-currency features for securitization and trading of the traded risk.

19. The computer system of claim 18, wherein the computer system further comprises sensors to generate updates of the technical process data.

20. The computer system of claim 1, wherein the processor is further configured to:
- calculate the monetary value of the technical impact, and
- continuously update the monetary value based on the updates from the one or more sensors.

* * * * *